(12) United States Patent
Hiemer et al.

(10) Patent No.: US 11,484,907 B2
(45) Date of Patent: Nov. 1, 2022

(54) APPLICATOR

(71) Applicant: SEITZ HIEMER SOGARO GBR, Bad Homburg (DE)

(72) Inventors: Andreas Hiemer, Ahrensburg (DE); Alberto C. Sògaro, Bad Homburg (DE); Sebastian Seitz, Dürrwangen (DE)

(73) Assignee: SEITZ HIEMER SOGARO GBR, Bad Homburg (DE)

( * ) Notice: Subject to any disclaimer, the term of this patent is extended or adjusted under 35 U.S.C. 154(b) by 0 days.

(21) Appl. No.: 17/055,386

(22) PCT Filed: May 16, 2019

(86) PCT No.: PCT/DE2019/100443
§ 371 (c)(1),
(2) Date: Nov. 13, 2020

(87) PCT Pub. No.: WO2019/219130
PCT Pub. Date: Nov. 21, 2019

(65) Prior Publication Data
US 2021/0220868 A1    Jul. 22, 2021

(30) Foreign Application Priority Data
May 16, 2018   (DE) ............... 10 2018 111 805.8

(51) Int. Cl.
*B05C 17/005*   (2006.01)
*A61M 5/24*   (2006.01)
(Continued)

(52) U.S. Cl.
CPC ...... *B05C 17/00593* (2013.01); *A61M 5/2466* (2013.01); *A61M 5/31511* (2013.01); *B05C 17/00586* (2013.01); *B05C 17/0133* (2013.01)

(58) Field of Classification Search
CPC .......... A61M 5/2466; A61M 51/31511; B05C 17/00586; B05C 17/0133; A61J 1/065
See application file for complete search history.

(56) References Cited

U.S. PATENT DOCUMENTS 3,739,947 A  *  6/1973  Baumann .............. A61M 5/284
                                                            222/136
4,329,376 A  *  5/1982  Szigeti ................. E01H 1/1213
                                                            134/4

(Continued)

FOREIGN PATENT DOCUMENTS

CA        2984531 A1    5/2018

OTHER PUBLICATIONS

PCT International Search Report and Written Opinion, PCT/DE2019/100443, dated Aug. 21, 2019, 17 pages.

*Primary Examiner* — Jeremy Carroll
(74) *Attorney, Agent, or Firm* — Quarles & Brady LLP (57) ABSTRACT

An applicator is proposed comprising an outer sleeve having a cylindrical inner surface and a receiving space for a flowable substance to be applied and an inner sleeve which can be displaced in the outer sleeve and in which a frangible ampule containing the flowable substance is disposed and which has an opening connecting an interior of the inner sleeve to the receiving space of the outer sleeve and an activation means upon whose activation the ampule breaks.

9 Claims, 12 Drawing Sheets

(51) Int. Cl.
*A61M 5/315* (2006.01)
*B05C 17/01* (2006.01)

(56) References Cited

U.S. PATENT DOCUMENTS

| | | | |
|---|---|---|---|
| 10,987,147 B2 * | 4/2021 | Vogt | A61B 17/8825 |
| 11,039,872 B2 * | 6/2021 | Vogt | B01F 15/0206 |
| 11,154,343 B2 * | 10/2021 | Vogt | A61M 5/19 |
| 2004/0162517 A1 * | 8/2004 | Furst | A61M 5/2046 |
| | | | 604/69 |
| 2009/0171361 A1 | 7/2009 | Melsheimer et al. | |
| 2014/0124534 A1 | 5/2014 | Gold | |
| 2015/0065992 A1 * | 3/2015 | Korkuch | A61M 5/31511 |
| | | | 604/506 |
| 2018/0093043 A1 | 4/2018 | McClellan et al. | |

* cited by examiner

APPLICATOR

CROSS-REFERENCE TO RELATED APPLICATIONS

This application claims priority to International Patent Application PCT/DE2019/100443, filed on May 16, 2019, which claims priority to German Patent Application DE 102018 111 805.8 filed on May 16, 2018, which applications are hereby incorporated herein by reference.

The disclosure relates to an applicator for applying a flowable substance, the applicator comprising a sleeve which is provided with a discharge opening via which the flowable substance can be applied.

Applicators of this kind are known from practice and serve, for example, for applying a medication or a cosmetic substance on the skin of a human or animal and also for applying any various substances, such as an adhesive. The applicator can be provided with a frangible ampule in which the flowable substance is contained. A precise dosing of the flowable substance is often not possible using the hitherto known applicators.

The object of the disclosure is to create an applicator by means of which the flowable substance contained in the frangible ampule can be conveyed to a discharge opening of the applicator in a defined manner.

According to the disclosure, the object is attained by the applicator having the features of claim 1.

According to the disclosure, an applicator is proposed which comprises an outer sleeve having a cylindrical inner surface and a receiving space for a flowable substance to be applied and an inner sleeve which is displaceable in the outer sleeve and in which a frangible ampule containing the flowable substance is disposed and which has an opening connecting an interior of the inner sleeve to the receiving space of the outer sleeve. Moreover, an activation means is provided upon whose activation the ampule breaks.

The applicator according to the disclosure consequently functions in such a manner that first the ampule is broken, causing the flowable substance to be freely contained in the interior of the inner sleeve. Via the opening, the flowable substance can flow from the interior of the inner sleeve into the receiving space of the outer sleeve and be applied via a discharge opening of the applicator according to its intended use.

The applicator according to the disclosure serves, for example, for applying a medication or a cosmetic substance on the skin of a human's or animal's body. Using the applicator in dentistry is also plausible. Furthermore, the applicator can be used for applying other various substances, such as adhesives or the like.

In a preferred embodiment of the applicator according to the disclosure, the activation means is made of a frontal insert of the inner sleeve, the insert being at least partially displaced into the inner sleeve and breaking the ampule. For instance, the inner sleeve is realized as a tube-like element having a cylindrical inner surface against which the activation means can be displaced. In particular, the frontal insert forming the activation means can be realized like a push button which is pushed into the inner sleeve manually, causing the ampule to be broken.

In a specific embodiment of the applicator according to the disclosure, the ampule, which is preferably an ampule having two tips which can be snapped off, is broken by a ramp of the activation means ascending on the ampule or one of the tips of the ampule.

In the inner sleeve, another ramp can be realized onto which the ampule or a tip of the ampule ascends upon actuation of the activation mans so that this tip is snapped off and the flowable substance to be applied can flow out.

For the flowable substance to flow into the receiving space after the ampule has been broken, the inner sleeve can be pulled out of the outer sleeve. This causes a negative pressure to be produced in the receiving space, whereby the flowable substance flows from the interior of the inner sleeve into the receiving space via the opening. A drain opening of the receiving space should obviously be closed which can be realized by means of a closing means or even by a check valve.

In a specific embodiment of the applicator according to the disclosure, the inner sleeve serves as a piston for discharging the flowable substance via a discharge opening. This means that the inner sleeve is displaced in the outer sleeve so as to apply the flowable substance when the flowable substance is disposed in the receiving space of the outer sleeve.

In a specific embodiment of the applicator according to the disclosure, a one-way valve is provided which prevents the flowable substance from flowing back into the inner sleeve from the receiving space. This embodiment enables the flowable substance to move from the interior of the inner sleeve into the receiving space of the outer sleeve by the inner sleeve being pulled from the outer sleeve and thus a negative pressure being generated in the outer sleeve or the receiving space of the outer sleeve, the negative pressure sucking the flowable substance from the inner sleeve into the receiving space of the outer sleeve via the opening.

In an inexpensively executable embodiment of the applicator according to the disclosure, the one-way valve is made of a rubbery-elastic plate which is fastened to a front side of the inner sleeve and interacts with the opening of the inner sleeve. The rubbery-elastic plate forms a piston surface when applying the substance by means of which the flowable substance is pushed out of the receiving space.

In order to be able to push the activation means in a defined manner, the inner sleeve comprises a guide track for the activation means in a specific embodiment of the applicator according to the disclosure. The guide track can be realized like slits. Correspondingly, a knub or a protrusion can be formed on the activation means, the knub or protrusion being disposed in the guide track and holding the activation means in the inner sleeve.

To facilitate use of the applicator according to the disclosure, the inner sleeve can have a collar or tabs for being gripped by a user. Accordingly, the outer sleeve can have a collar or tabs against which a user's fingers abut.

Another specific embodiment of the applicator according to the disclosure has a second receiving space which is divided from the receiving space via an opening and a second check valve. This receiving space is an application space in which a piston can be displaceably stored for applying the flowable substance.

For actuating the applicator according to the disclosure, an actuation device can be provided which displaces the piston with respect to the outer sleeve. For instance, the outer sleeve engages in a thread via a thread, the former thread being disposed in a stationary manner in the axial direction with respect to an applicator casing. When the actuation device is actuated, the thread disposed axially in a stationary manner with respect to the applicator casing is turned so that the outer sleeve is displaced and the piston is pushed into the application space. Owing to this, the flowable substance contained in the application space is discharged via a discharge opening.

Further advantages and advantageous embodiments of the subject matter of the disclosure are derived from the description, the drawing and the patent claims.

Exemplary embodiments of an applicator according to the disclosure are illustrated in the drawing in a schematically simplified manner and are described in further detail in the following description.

In FIGS. 1 to 7 an applicator is 1 illustrated which serves for applying a flowable substance, such as medication, a cosmetic substance or an adhesive. Applicator 1 comprises an outer sleeve 10 on which a discharge opening 11 is formed on the front side and on which a collar 12, which serves as a gripping aid, is formed on the end facing away from the discharge opening. Outer sleeve 10 has a cylindrical inner surface on which an inner sleeve 15 is guided. Inner sleeve 15 receives a frangible ampule 16, which is made of glass and has two points 17 and 18 which can be snapped off, in the delivery state of applicator 1 illustrated in FIGS. 1, 2 and 4.

Figure 4:
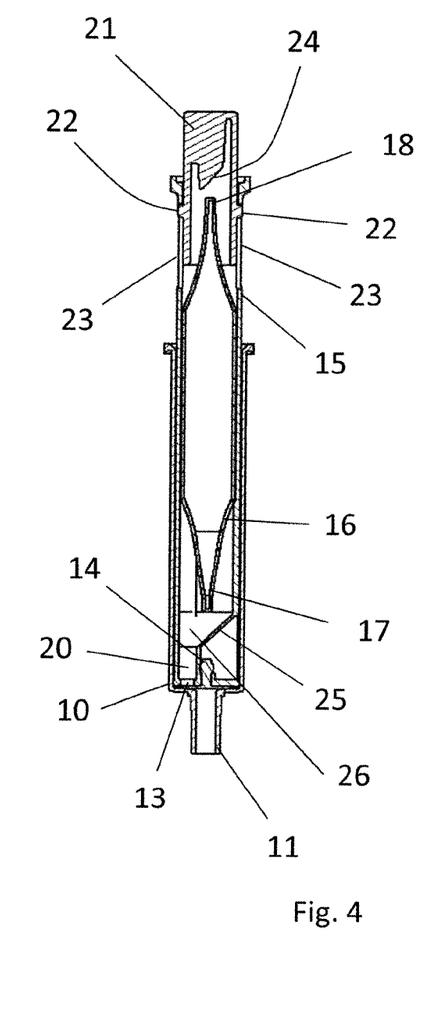
FIG. 4 shows a longitudinal cut through the applicator along line A-A in FIG. 2.

At its opening facing discharge opening 11, inner sleeve 15 comprises an opening 20 which is provided with a check valve 13 consisting of a mushroom-shaped rubber element whose head forms the sealing element for opening 20 and abuts against the front side of inner sleeve 15. A foot 14 of check valve 13 is inserted into a frontal hole of inner sleeve 15 and thus holds check valve 13 on inner sleeve 15. Moreover, inner sleeve 15 has a collar 27 serving as a gripping aid at its end facing away from opening 20.

Furthermore, applicator 1 comprises an activation means 21 which consists of a frontal, push-button-like insert of inner sleeve 15 and can be displaced in a cylindrical interior of inner sleeve 15. On its circumference, the activation means has two knubs 22 which are placed at a 180° offset to one another and each engage in a guide track 23, which is formed on inner sleeve 15 and extends along the length of applicator 1.

Push-button-like activation means 21 has a ramp 24 on its inner side, ramp 24 ascending on tip 18 of ampule 16 upon activation of activation means 21 and snapping tip 18 off. Moreover, a ramp 25 is formed adjacent to opening 20 in inner sleeve 15, ramp 25 interacting with tip 17 of ampule 16 and serving to snap off tip 17 and opening ampule 16 upon activation of activation means 21 and opening ampule 16. Furthermore, inner sleeve 15 comprises an interior 26 which receives ampule 16 and is connected to a receiving space 28 via opening 20, receiving space 28 being disposed in outer sleeve 10 between the front side of inner sleeve 15 or check valve 13 on the one hand and discharge opening 11 on the other hand.

Applicator 1 illustrated in FIGS. 1 to 7 functions in the manner described below.

Figure 1:
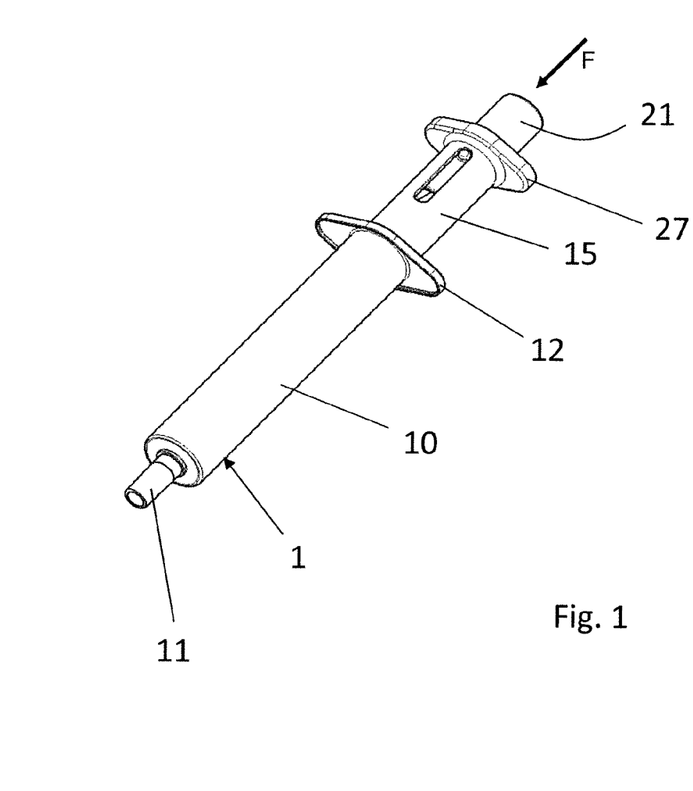
FIG. 1 is a perspective view of an applicator according to the disclosure.
Figure 2:
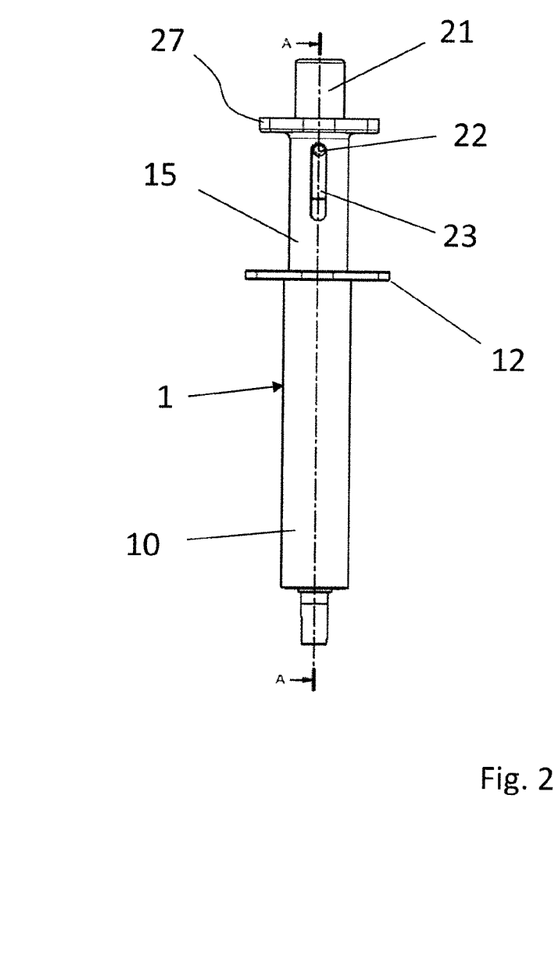
FIG. 2 is a side view of the applicator according to FIG. 1.
Figure 3:
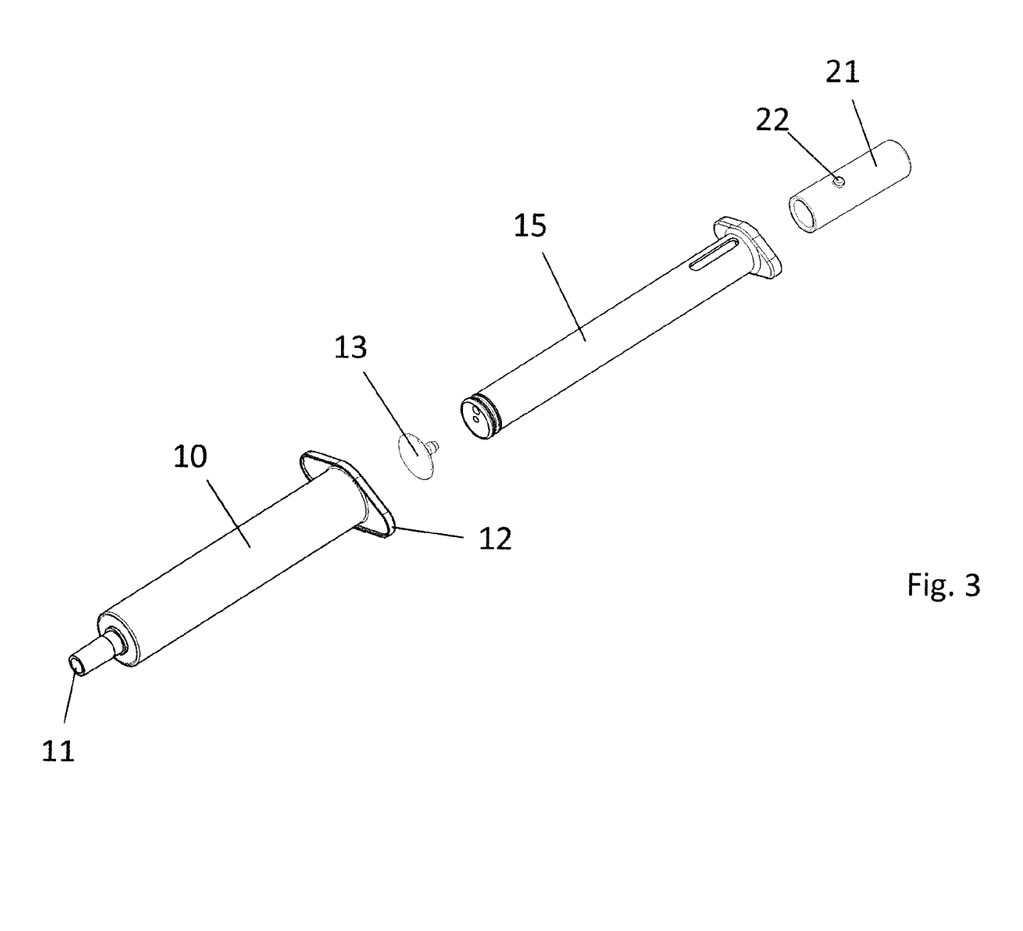
FIG. 3 shows the applicator according to FIG. 1 in a disassembled state.
Figure 5:
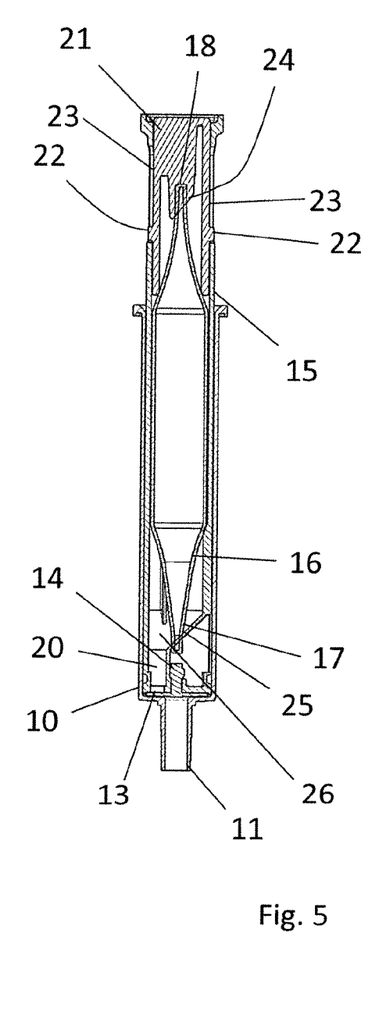
FIG. 5 shows a longitudinal cut through the applicator according to FIG. 4, but after an activation means has been activated.
Figure 6:
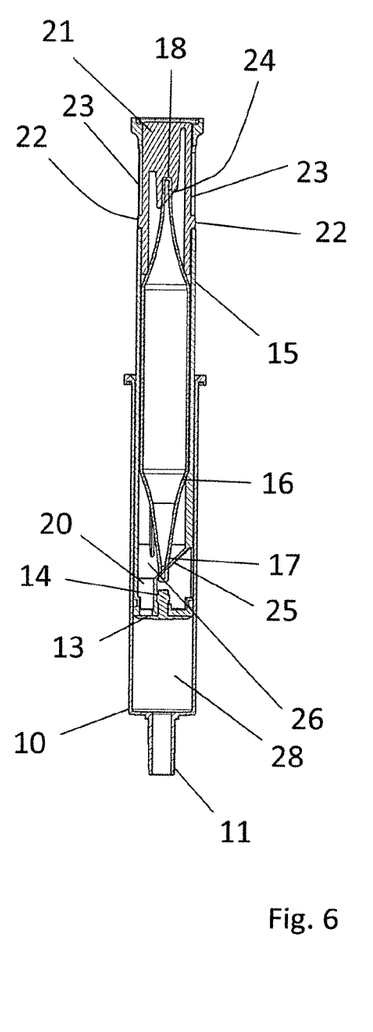
FIG. 6 shows a longitudinal cut through the applicator according to FIG. 5, but in the application state.
Figure 7:
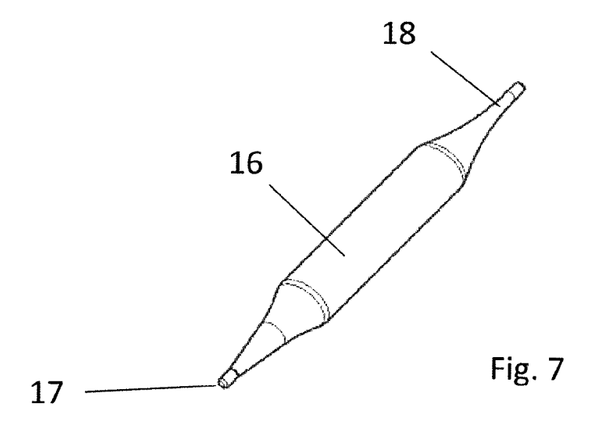
FIG. 7 is a perspective view of a frangible ampule of the applicator.
Figure 8:
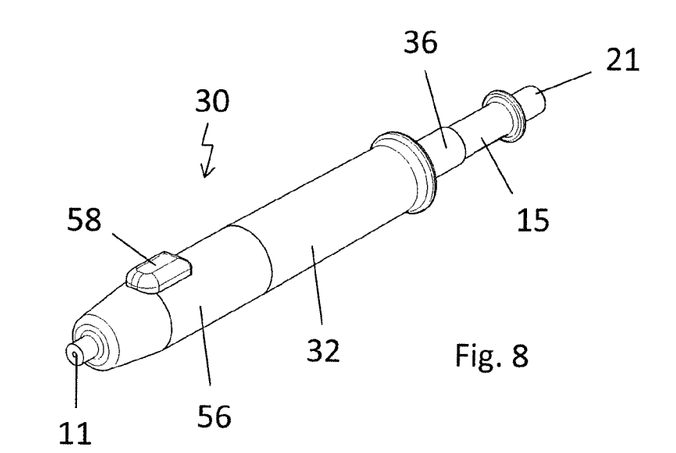
FIG. 8 is a perspective view of a second embodiment of an applicator according to the disclosure.
Figure 9:
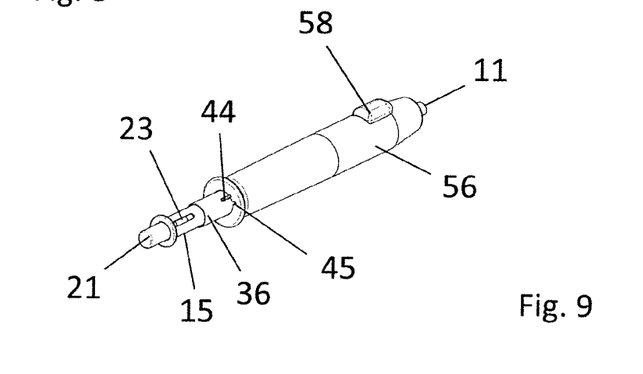
FIG. 9 is a second perspective view of the applicator according to FIG. 8.
Figure 10:
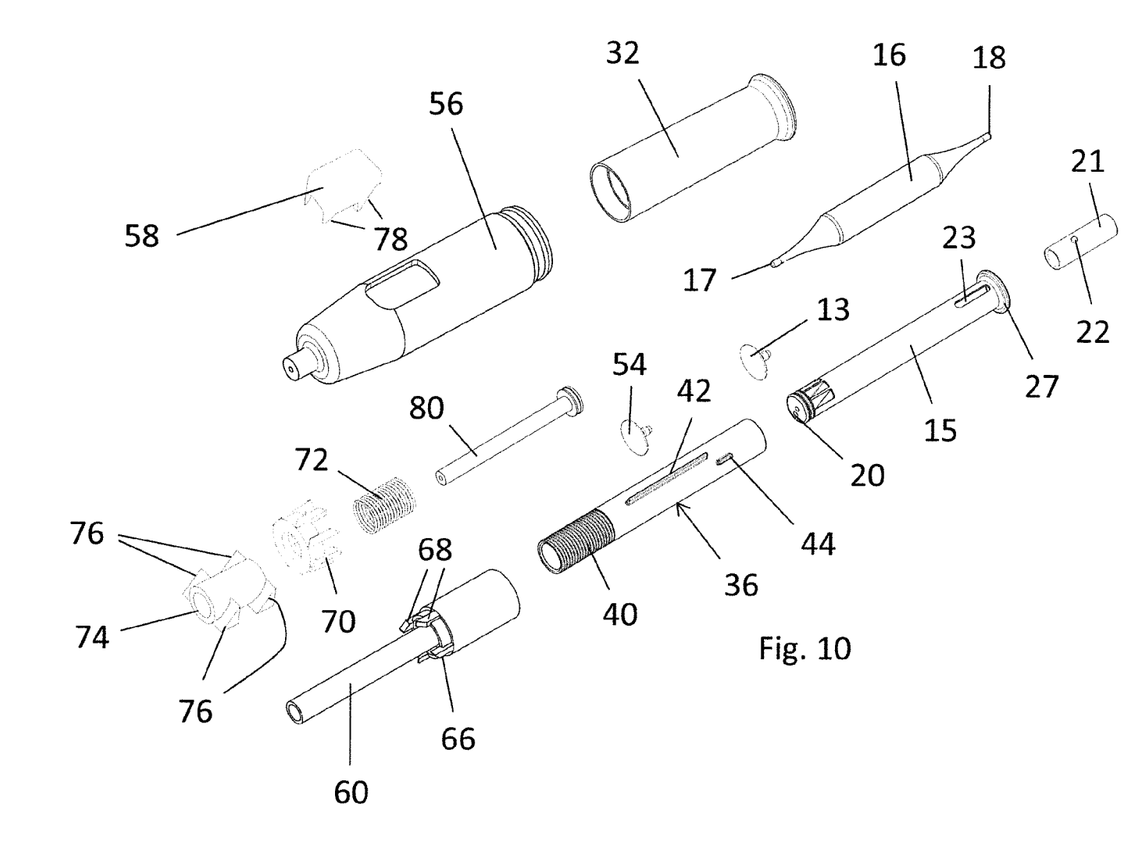
FIG. 10 is an overview of the individual parts of the applicator according to FIGS. 8 and 9.

With the delivery state illustrated in FIGS. 1, 2 and 4 serving as the starting point when using applicator 1, push-button-like activation means 21 is first pushed into inner sleeve 15 according to FIG. 5, whereby ramp 24 ascends on tip 18 of ampule 16 and ampule 16 is pushed against ramp 25 of inner sleeve 15 by its tip 17. Owing to this, both tips 17 and 18 are snapped off and the flowable substance contained in ampule 16 can flow into interior 26 of inner sleeve 15. In a subsequent step, the inner sleeve disposed in outer sleeve 10 is slightly pulled out in the direction facing away from discharge opening 11, which remains closed by means of a lid, a check valve or the like. Receiving space 28 consequently becomes larger between the front side of inner sleeve 15 and discharge opening 11, the flowable substance contained in the inner sleeve being conveyed into receiving space 28 via opening 20, which is provided with the check valve or one-way valve, due to the arising negative pressure in receiving space 28. Applicator 1 is consequently in an application state. By exerting a force F on the backmost front side of inner sleeve 15 (the front side being formed by activation means 21, and inner sleeve 15 serving as a piston), the liquid contained in receiving space 28 can now be conveyed and applied from applicator 1 via now open discharge opening 11 which can be provided with a one-way valve or check valve.

In FIGS. 8 to 14 an applicator 30 is illustrated which also serves for applying a flowable substance via a discharge opening 11. Applicator 30 comprises an applicator casing 32 which comprises an essentially cylindrical reception 34 in which an outer sleeve 36 is disposed. Outer sleeve 36 comprises a cylindrical circumferential wall 38 provided in an end section with an external thread 40. Moreover, guide ribs 42 are formed on circumferential wall 38 which extend in the axial direction and are guided on the interior of applicator casing 32. Placed at an offset in the circumferential direction, two abutment ribs 44 are formed on circumferential wall 38 of outer sleeve 36, both abutment ribs 44 interacting with front side 46 or a guide groove 47 of applicator casing 32 depending on the state and serving as an anti-rotation means of receiving sleeve 36 when applying the flowable substance.

Figure 11:
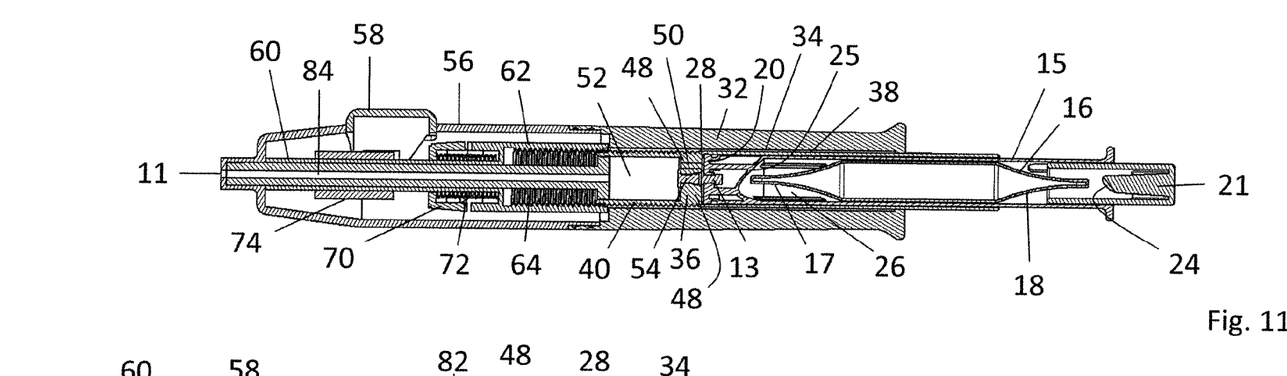
FIG. 11 shows a longitudinal cut through the applicator in its delivery state according to FIGS. 8 and 9.
Figure 12:
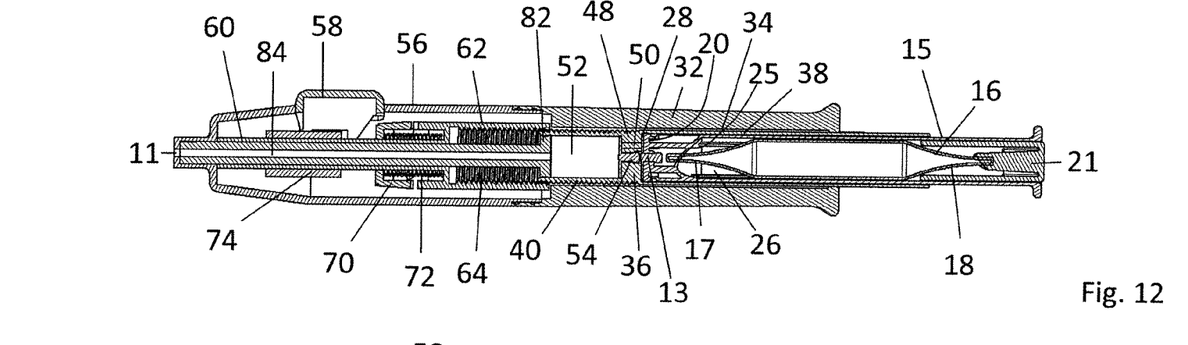
FIG. 12 shows a longitudinal cut through the applicator according to FIG. 11, but after the activation means has been activated.
Figure 13:
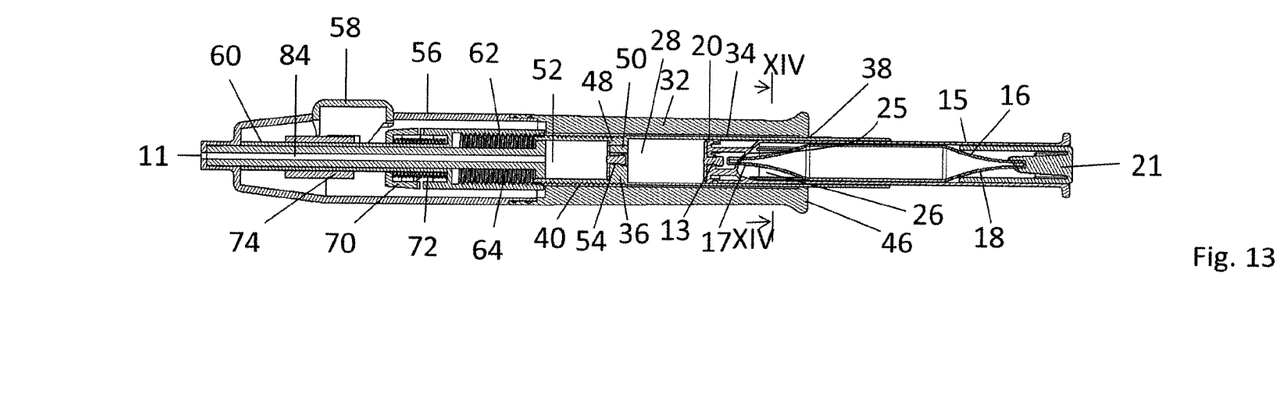
FIG. 13 also shows a longitudinal cut through the applicator according to FIG. 11, but after a receiving space of the applicator has been filled.
Figure 14:
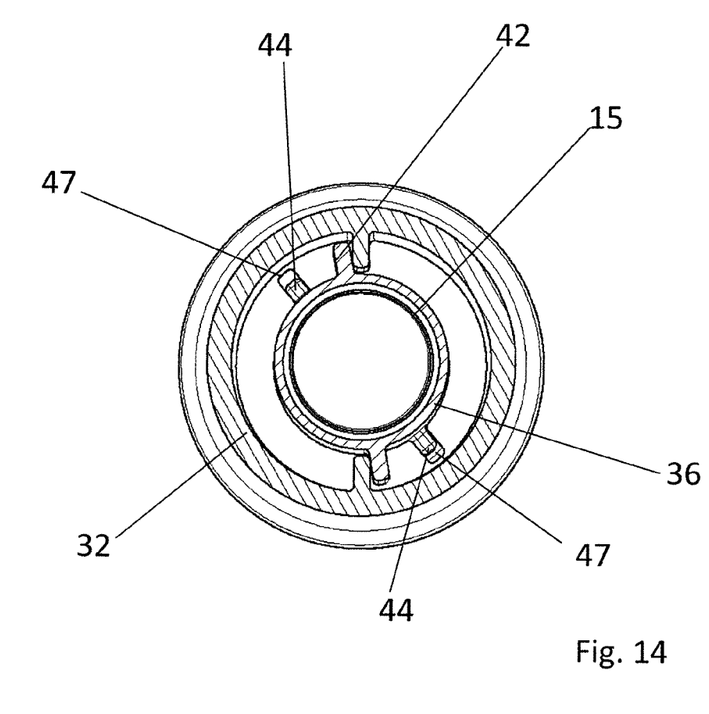
FIG. 14 shows a cut through the applicator along line XIV-XIV in FIG. 13.
Figure 15:
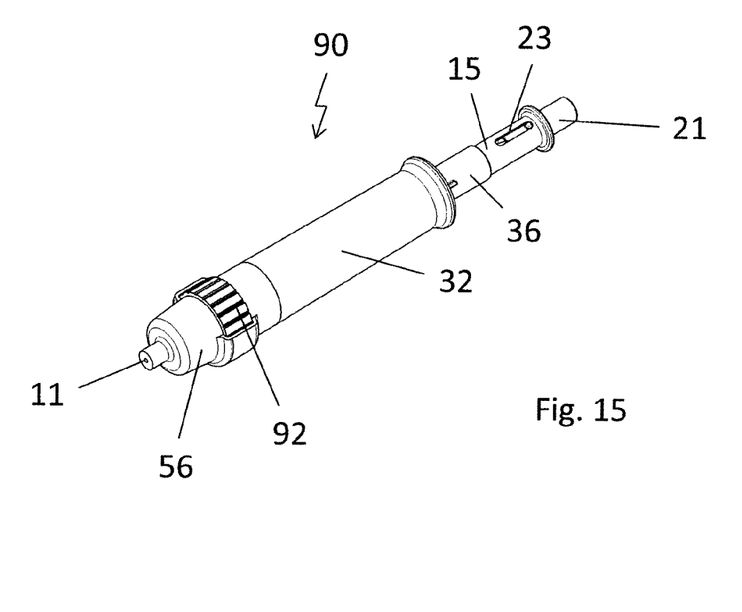
FIG. 15 is a perspective view of a third embodiment of an applicator according to the disclosure.
Figure 16:
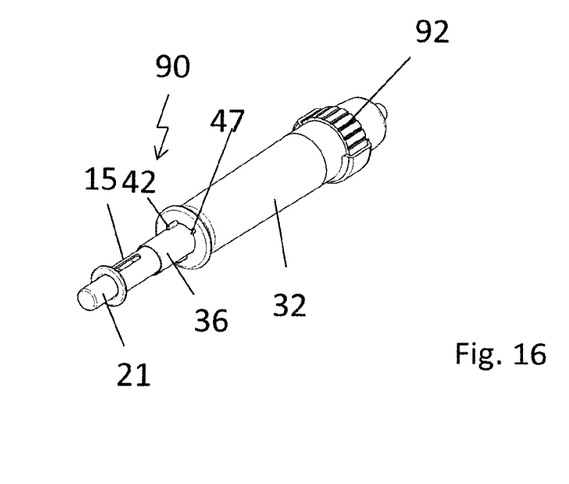
FIG. 16 is another perspective view of the applicator according to FIG. 15.
Figure 17:
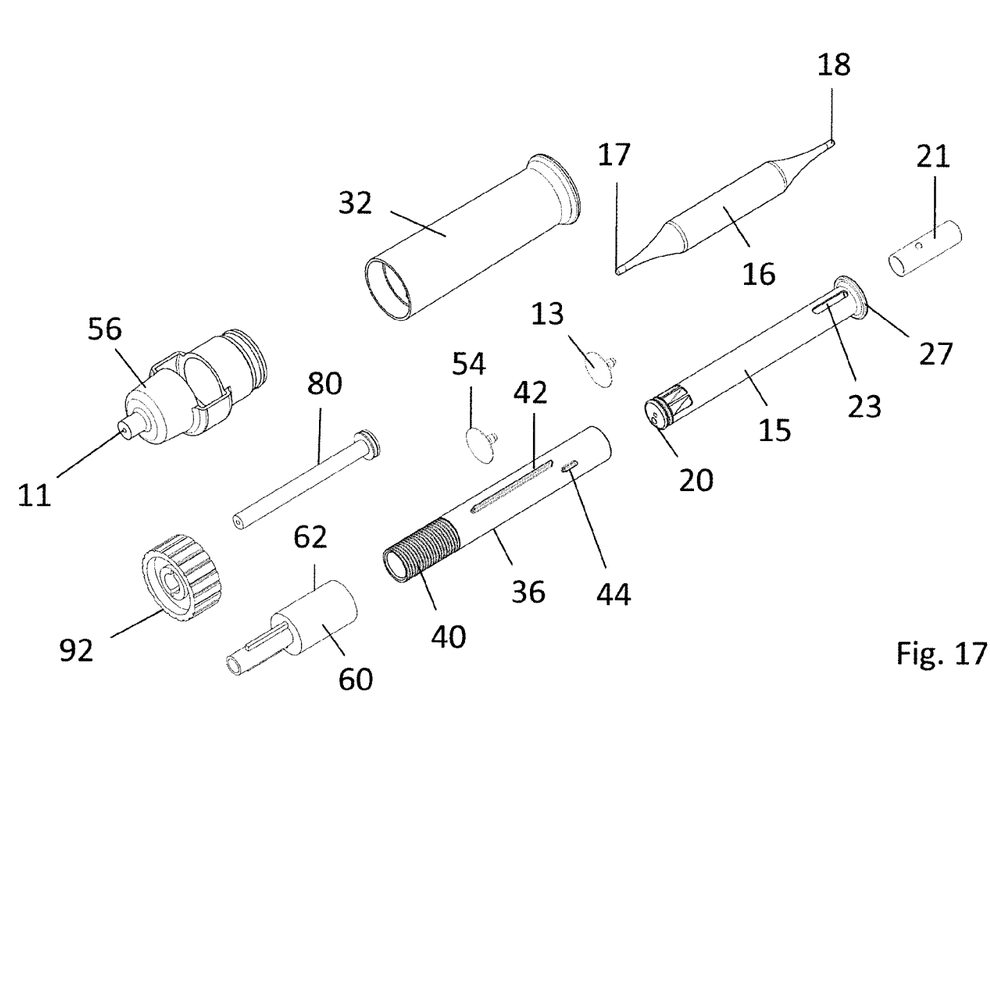
FIG. 17 is a perspective view of the individual parts of the applicator according to FIGS. 15 and 16.
Figure 18:
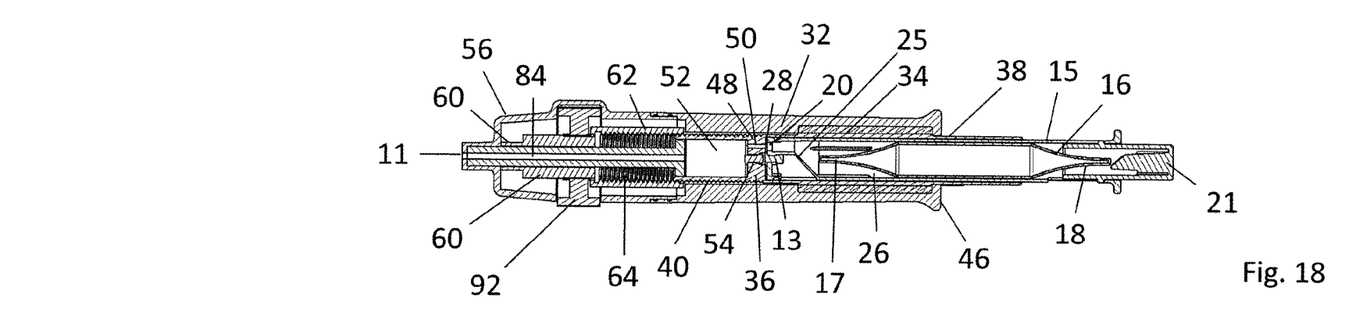
FIG. 18 shows a longitudinal cut through the applicator in its delivery state according to FIGS. 15 and 16.
Figure 19:
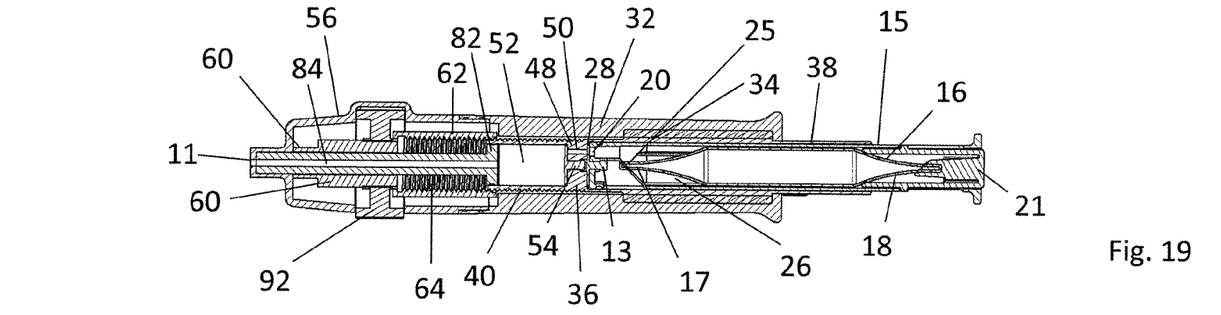
FIG. 19 shows a longitudinal cut through the applicator according to FIG. 18, but after an activation means has been activated.
Figure 20:
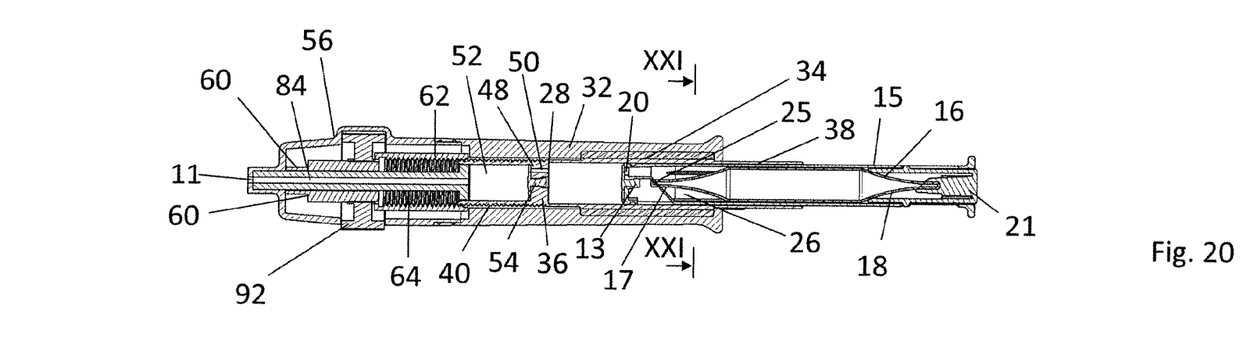
FIG. 20 shows a longitudinal cut through the applicator according to FIG. 18, but after a receiving space of the applicator has been filled.
Figure 21:
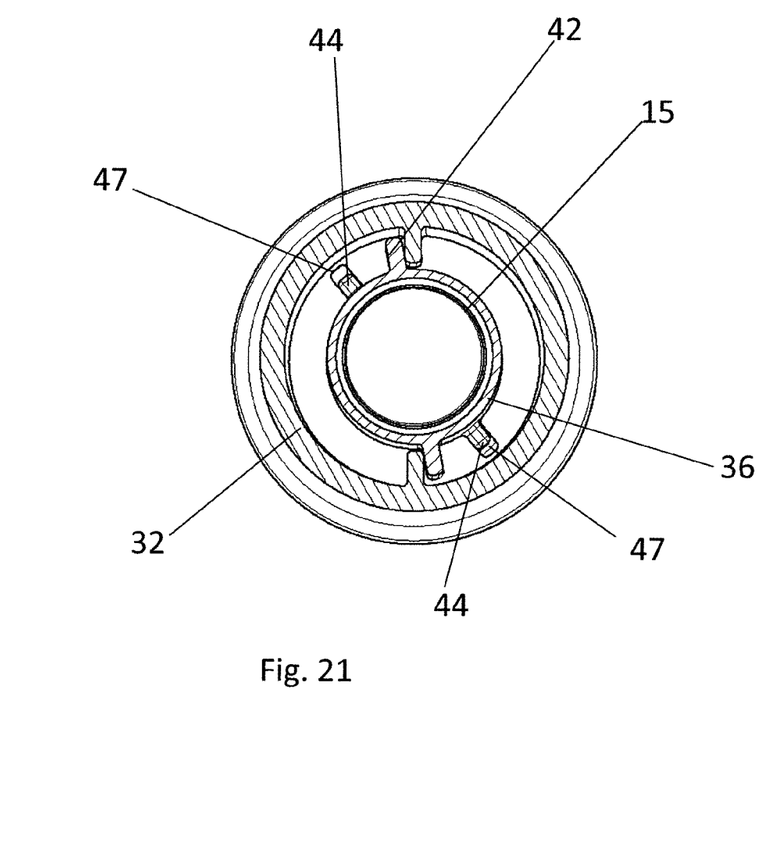
FIG. 21 shows a cut through the applicator according to FIG. 20 along line XXI-XXI in FIG. 20.

Outer sleeve 36 comprises a dividing wall 48 in which a connecting channel 50 is formed which connects a receiving space 28 facing away from discharge opening 11 to a receiving space 52 facing toward discharge opening 11. In receiving space 28 of outer sleeve 36, an inner sleeve 15 engages which is realized according to the embodiment of the inner sleeve illustrated in FIGS. 1 to 7, for which reason reference is made to the description of inner sleeve 15 in conjunction with this embodiment. Inner sleeve 15 consequently receives a frangible ampule 16 having two tips 17 and 18 which can be snapped off. Moreover, an activation means 21 in the form of a push-button-like insert is inserted into the front side of inner sleeve 15 facing away from the discharge opening, the insert comprising a ramp 24 on its interior. Furthermore, a check valve 13, which is realized according to the check valve of the embodiment illustrated in FIGS. 1 to 7, is disposed on the front side facing toward outer sleeve 36.

Connecting channel 50, which is formed in dividing wall 48 of outer sleeve 36, interacts with another check valve 54 which consists of a mushroom-shaped rubber element corresponding to check valve 13, the rubber foot of check valve 54 being held in a hole of dividing wall 48.

Applicator casing 32 has a frontal casing attachment 56 provided with a push button 58 which can be displaced in the radial direction with respect to casing attachment 56 in relation to the axis of applicator 30. Discharge opening 11 is formed on casing attachment 56. Moreover, casing attachment 56 receives an application tube 60 which supports itself on casing attachment 56 by its front face facing away from inner sleeve 15 and has an extension 62 on which an inner thread 64 is formed which engages with outer thread 40 of outer sleeve 36. On a step 66 of extension 62 facing away from inner sleeve 15, actuating ramps 68 are formed which interact with an actuating collar 70 in the same manner as when a pen is actuated, actuating collar 70 comprising counter ramps and being disposed on application tube 60 in a rotatable manner. A return spring 72 is spanned between actuating collar 70 and extension 62 of application tube 60. A slider 74 is displaceably stored on application tube 60, slider 74 interacting with counter ramps 78, which are disposed on push button 58, via actuation ramps 76. By actuating ramps 76 interacting with counter ramps 78, slider 74 is displaced against actuating collar 70 when pushing push button 58 in the axial direction of applicator 30 so that actuating collar 70 interacts with actuating ramps 68 via its counter ramps, causing application tube 60 to be turned and outer thread 40 of outer sleeve 36 to be turned in inner thread 64 of application tube 60.

A piston tube 80 engages through application tube 60, one of the front sides of piston tube 80 supporting itself on casing attachment 56 in the area of discharge opening 11 and the other front side being formed by an annular collar 82 which forms a piston surface.

Applicator 30 illustrated in FIGS. 8 to 14 functions in the manner described below.

With the delivery state illustrated in FIG. 11 as the starting point, activation device 21 is first activated in such a manner that tips 17 and 18 of ampule 16 are snapped off and the liquid contained in ampule 16 can flow into interior 26 of inner sleeve 15. Subsequently, inner sleeve 15 is slightly pulled out of outer sleeve 36, whereby receiving space 28 is enlarged between dividing wall 48 and the front face of inner sleeve 15 and the liquid being sucked out of interior 26 of inner sleeve 15 into receiving space 28 owing to the resulting vacuum (cf. FIG. 13). Subsequently, the unit consisting of inner sleeve 15 and activation means 21 is pushed into outer sleeve 36 like a piston, causing the liquid to be pushed out of receiving space 28 into receiving space 52 via connecting channel 50. Then, outer sleeve 36 can be turned with respect to applicator casing 32, releasing abutment ribs 44 and letting them dip into guide grooves 47 of applicator casing 32. Applicator 30 is now activated. By pushing push button 58, application tube 60 is turned in the manner described above so that outer sleeve 36 is turned into extension 62 of application tube 60. Owing to this, piston tube 80 squeezes the liquid from receiving space 52 through piston channel 84 to discharge opening 11, via which the liquid can be applied.

In FIGS. 15 to 21, an applicator 90 is illustrated which for the most part corresponds to the applicator according to FIGS. 8 to 14 but differs in the respect that it comprises an application tube 60 which can be actuated by means of an actuating ring 92 rotatable in the circumferential direction of applicator 90. By actuating ring 92 being actuated, application tube 60, through which piston tube 80 engages, is turned so that outer thread 40 of outer sleeve 36 is turned into inner thread 64 of extension 62 of application tube 60. Piston tube 80 squeezes the liquid contained in receiving space 52 of outer sleeve 36 to discharge opening 11.

In all other respects, applicator 90 corresponds to the one illustrated in FIGS. 8 to 14.

Figure 22:
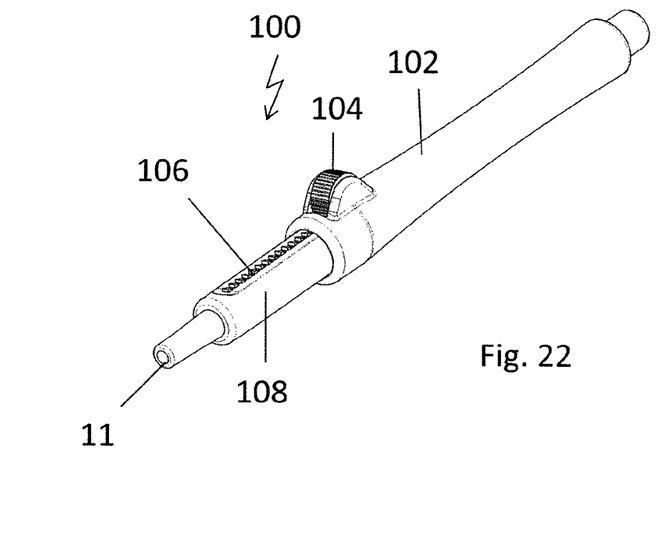
FIG. 22 is a perspective view of a fourth embodiment of an applicator according to the disclosure.

In FIG. 22, an applicator 100 is illustrated which for the most part corresponds to the applicator according to FIGS. 15 to 21 but differs in the respect that it comprises an applicator casing 102 provided with an actuating wheel 104 which interacts with an axial toothing 106 formed on an application tube 108 which is guided on an outer sleeve in a sliding manner, the outer sleeve corresponding to the outer sleeve of the embodiment according to FIGS. 15 to 21 but does not comprise an outer thread. By the actuating wheel 104 being actuated, application tube 108 is displaced on the outer sleeve in conjunction with a piston tube 80, which is received by application tube 108, so that the liquid is applied via a discharge opening 11.

LIST OF REFERENCE NUMERALS 1 applicator
10 outer sleeve
11 discharge opening
12 collar
13 check valve
14 foot
15 inner sleeve
16 ampule
17 tip
18 tip
20 opening
21 activation means
22 knubs
23 guide track
24 ramp
25 ramp
26 interior 27 collar
28 receiving space
30 applicator
32 applicator casing
34 reception
36 outer sleeve
38 circumferential wall
40 outer thread
42 guide ribs
44 abutment ribs
46 front side
47 guide grooves
48 dividing wall
50 connection channel
52 receiving space
54 check valve
56 casing attachment
58 push button
60 application tube
62 extension
64 inner thread
66 step
68 actuating ramp
70 actuating collar
72 return spring
74 slider
76 actuating ramp
78 counter ramp
80 piston tube
82 ring collar
84 piston channel
90 applicator
92 actuating ring
100 applicator
102 applicator casing
104 actuating wheel
106 axial toothing
108 application tube

The invention claimed is:

1. An applicator comprising an outer sleeve having a cylindrical inner surface and a receiving space for a flowable substance to be applied and an inner sleeve comprising a first planar ramp which is displaceable in the outer sleeve and in which a frangible ampule having first and second tips and containing the flowable substance is disposed and which has an opening connecting an interior of the inner sleeve to the receiving space of the outer sleeve, as well as comprising an activation means comprising a second planar ramp, wherein upon activation of the activation means, the first tip of the ampule ascends on the first planar ramp and the second planar ramp of the activation means ascends on the second tip of the ampule, snapping off the first and second tips.

2. The applicator according to claim 1, wherein the activation means is a frontal insert of the inner sleeve which is partially displaced into the inner sleeve upon activation and breaks the ampule.

3. The applicator according to claim 1, wherein a negative pressure is generable in the receiving space as a consequence of displacing the inner sleeve in the outer sleeve so that the flowable substance contained in the interior of the inner sleeve flows into the receiving space via the opening.

4. The applicator according to claim 1, wherein the inner sleeve serves as a piston for discharging the flowable substance via the discharge opening.

5. The applicator according claim 1, further comprising a check valve which prevents the flowable substance from flowing back into the inner sleeve from the receiving space.

6. The applicator according to claim 5, wherein the check valve is made of a rubbery-elastic plate which is fastened to a front side of the inner sleeve and interacts with the opening of the inner sleeve.

7. The applicator to claim 1, wherein the inner sleeve has a guide track for the activation means.

8. The applicator according to claim 1, wherein the inner sleeve has a collar for being gripped by a user.

9. The applicator according to claim 1, wherein the outer sleeve has a collar against which a user's fingers abut.

* * * * *